(12) United States Patent
Mercereau

(10) Patent No.: US 6,409,663 B1
(45) Date of Patent: Jun. 25, 2002

(54) APPARATUS AND METHOD FOR MONITORING THE VITAL STATUS OF BIOLOGICAL MATERIALS

(76) Inventor: Steven F. Mercereau, 4911 W. Lake Dr., Conyers, GA (US) 30208

( * ) Notice: Subject to any disclaimer, the term of this patent is extended or adjusted under 35 U.S.C. 154(b) by 0 days.

(21) Appl. No.: 09/439,873

(22) Filed: Nov. 12, 1999

(51) Int. Cl.[7] ................................. A61B 5/00
(52) U.S. Cl. ..................................... 600/300
(58) Field of Search ................. 600/300, 595, 600/549, 341; 368/10; 340/573.1; 128/898, 899

(56) References Cited

U.S. PATENT DOCUMENTS

| | | | |
|---|---|---|---|
| 4,819,860 A | * 4/1989 | Hargrove et al. ........... 600/549 |
| 4,995,399 A | 2/1991 | Hayashi et al. ............. 128/680 |
| 5,080,105 A | 1/1992 | Thornton ..................... 128/670 |
| 5,271,410 A | 12/1993 | Wolzinger et al. ........... 128/692 |
| 5,285,796 A | 2/1994 | Hughes ....................... 128/668 |
| 5,337,290 A | * 8/1994 | Ventimiglia et al. .......... 368/10 |
| 5,355,889 A | 10/1994 | Nevo et al. .................. 128/671 |
| 5,370,122 A | 12/1994 | Kunig et al. ................. 128/670 |
| 5,615,685 A | * 4/1997 | Suga ........................... 600/300 |
| 5,873,369 A | * 2/1999 | Laniado et al. .............. 600/300 |
| 5,941,837 A | * 8/1999 | Amano et al. ............... 600/595 |
| 5,964,701 A | * 10/1999 | Asada et al. ................. 600/300 |
| 6,122,536 A | * 9/2000 | Sun et al. .................... 600/341 |
| 6,198,394 B1 | * 3/2001 | Jacobsen et al. ......... 340/573.1 |

* cited by examiner

Primary Examiner—Kevin Shaver
Assistant Examiner—Brian Szmal
(74) Attorney, Agent, or Firm—Baker, Donelson, Bearman & Caldwell

(57) ABSTRACT

An apparatus for monitoring the vital status of a biological material in which a pair of sensors are held in a housing for sensing separate respective stimulus of a biological material. A controller operatively communicates with the pair of sensors for receiving signals reflective of the respective stimulus measured by the sensors. An evaluator generates a status signal representative of the state of the biological material based on the signals, and a reporter displays the status signal, so that the vital status of the biological material can be monitored. A method of monitoring the vital status and adjusting delivery of a medicant is disclosed.

15 Claims, 2 Drawing Sheets

APPARATUS AND METHOD FOR MONITORING THE VITAL STATUS OF BIOLOGICAL MATERIALS

TECHNICAL FIELD

The present invention relates to apparatus and methods of evaluating the status of vital life activity of biological materials. More particularly, the present invention relates to apparatus and methods of evaluating and monitoring stimuli of vital life activity of biological materials for diagnosis, monitoring, and treatment.

BACKGROUND OF THE INVENTION

In studying the dynamics of changes in materials and substances made up of groups or systems that are comprised of numerous similar units, scientists have relied on measuring state variables of the groups. These state variable include pressure, volume, temperature, and internal energy of a group or system, and related to time and spatial relationships (position) of the units in the group. Another state variable known as entropy can be determined with the measured pressure and temperature state variables in combination with temporal relationship, but heretofore the entropy state variable has not been used in studying the vitality of biological material.

Entropy can be defined as the number of possible arrangements for the units in the group being studied relative to position and velocity of the units of the group. Because entropy is a state variable, entropy evaluations provides information in thermodynamics analysis useful to describe the groups, systems and processes being observed. Under identical conditions, a system or group always has the same entropy.

It is known by observation that living things, which by definition are continually changing and growing in a demonstrated cyclical fashion, have various degrees of health or vitality associated with their state. State variables, such as temperature and pressure, fluctuate relative to the vitality of the thing. The entropy of a living thing also fluctuates, because entropy essentially dictates the relationship between the temperature and the pressure of the group during a temporal period. Entropy in some way may therefore be considered as bridging between temperature and pressure. The changes in the arrangement of the units in the group and the other possible arrangements of the group (its entropy) produce the measurable temperature and pressure of the group. Entropy can be considered a bridge between the heat component (temperature) and the work component (pressure) of the total energy of the group. As noted above, under identical conditions a system or group has the same entropy. Accordingly, the vitality of a dynamic living group correlates to the entropy of the living group and changes in entropy correlate to changes in vitality of the living group.

Measuring the entropy and changes in entropy while the life processes progress provides information useful to a better understanding of the health and vitality of living things, because entropy measurements reflect the actual changes taking place in the living group, rather than the consequences of the changes.

Life functions are supported by various cycles of oxidation and reduction as described in the Krebs cycle. Life functions are maintained and reproduced through divisions of cells and chromosomes and replication of organized structures such as DNA and RNA as described in the Watson and Crick model. The nature of these cycles defines organized and repeated states at the cellular level. The proper progression of these processes requires organized groups. Because all processes have some degree of tolerance, significant fluctuations, as well as subtle differences, from normal or optimum organization or entropy in the living group can provide early indications of malfunctions. Heretofore, it has not been recognized that monitoring of the entropy or organization of the group can be used in diagnosis, prognosis and developing and monitoring therapies or treatments for living groups.

Nature has a preferred direction for the course of spontaneous events, which is described in the second law of thermodynamics. That is, when left alone, groups tend to seek the lowest state of energy and the highest state of disorder. In terms of entropy, the second law may be expressed—if an isolated system undergoes a change, the system will change in such a way that the entropy of the system will increase or at best, remain constant. This can be re-stated as—if a system is allowed to undergo spontaneous change, the system will change in such a way that its disorder will increase, or at best, not decrease. For example, a dead body decays and turns to dust; but the elements do not spontaneously reform the body in the reverse process. Life vitality is the property of plants and animals that allows them to take in food, get energy from it, grow, adapt themselves to their surroundings and reproduce themselves—in essence, build order or reduce entropy. Considered in light of the second law of thermodynamics, living materials behave differently then dead materials relative to entropy and yet heretofore, entropy has not been measured or evaluated in monitoring the vital status of living things.

Accordingly, there is a need in the art for an improved method and apparatus for monitoring and evaluating the vital status of biological materials for health monitoring, diagnosis, and treatment. It is to such that the present invention is directed.

BRIEF SUMMARY OF THE PRESENT INVENTION

The present invention meets the need in the art by providing an apparatus for monitoring a vital status indicator of a biological material, in which a temperature sensor senses periodically a temperature of a biological material to be monitored for determining an indicator of a vital status of the biological material, the temperature sensor adapted to create a first electrical signal representative of the sensed temperature, and a pressure sensor senses periodically a pressure of the biological material substantially contemporaneously with the sensing by the temperature sensor, the pressure sensor adapted to create a second electrical signal representative of the sensed pressure. A signal transmitting pathway transmits the first and second electrical signals to a signal receiver adapted to receive at least two of the first and second electrical signals for processing of the signals. An evaluator compares the difference in the two first electrical signals representative of temperatures sensed at a first time and a second time with the difference in the two second electrical signals representative of the pressures sensed, to determine the indicator of the vital status as a representative value indicative of the state of the biological material. A reporter communicates the indicator of the vital status of the biological material, for monitoring the vital status of the biological materially.

In another aspect, the present invention provides a method of diagnosing the vital status of a biological material, comprising the steps of:

(a) providing a temperature sensor for sensing periodically a temperature of a biological material to be monitored for determining an indicator of a vital status of the biological material, said temperature sensor adapted to create a first electrical signal representative of the sensed temperature;

(b) providing a pressure sensor for sensing periodically a pressure of the biological material and adapted to create a second electrical signal representative of the sensed pressure substantially contemporaneously with the sensing by the temperature sensor;

(c) communicating by a signal transmitting pathway said first and second electrical signals to a signal receiver adapted to receive at least two of said first and second electrical signals for processing of the signals;

(d) comparing the difference in the two first electrical signals representative of temperatures sensed at a first time and a second time with the difference in the two second electrical signals representative of the pressures sensed, to determine the indicator of the vital status as a representative value indicative of the state of the biological material; and (e) reporting the indicator of the vital status of the biological material, whereby the vital status of the biological material can be monitored.

Objects, advantages and features of the present invention will become apparent from a reading of the following detailed description of the invention and claims in view of the appended drawings.

DETAILED DESCRIPTION OF THE PREFERRED EMBODIMENTS

Figure 1:
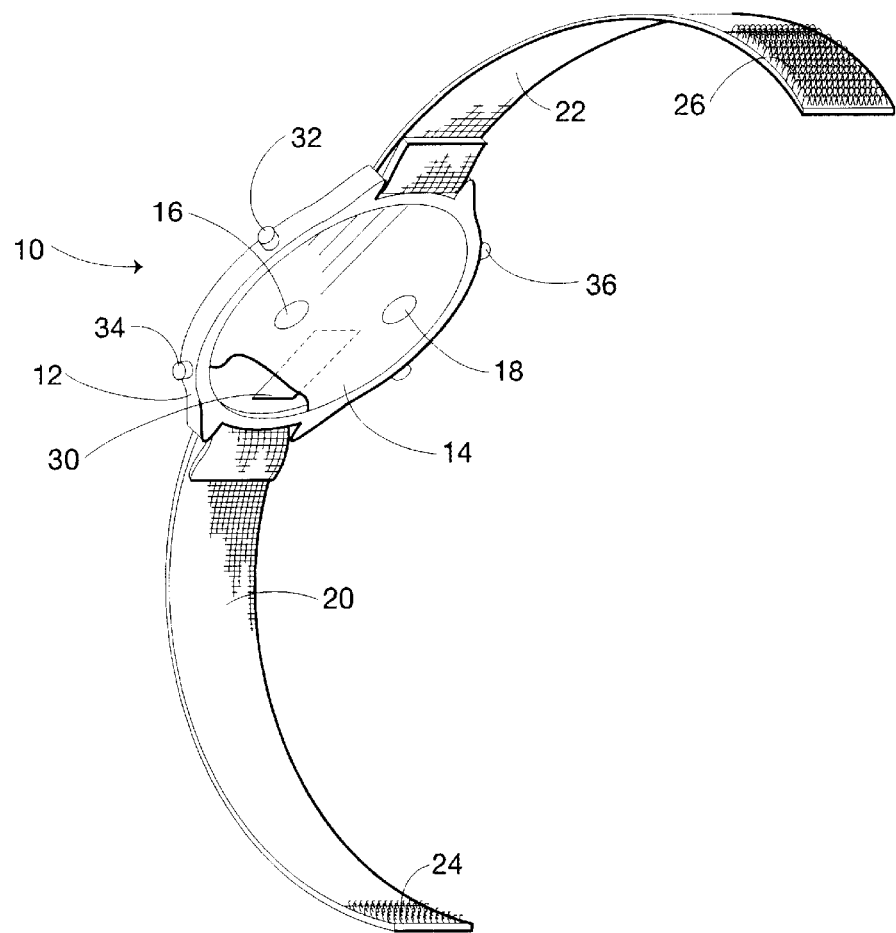
FIG. 1 illustrates a perspective view of a back side of a measuring and display apparatus according to the present invention.

In accordance with the present invention, entropy of a group under examination is measured and compared with standards as an indicator of the vital status of the group. The measuring of the entropy of biological materials provides a vital status indicator that can be used for diagnosis, prognosis, and monitoring and improving treatments and therapies. Accordingly, the present invention provides methods and apparatus of measuring the entropy of biological materials. The method according to the present invention makes basic assumptions and provides only a general measure of entropy. However, the measuring and monitoring of entropy allows an observer insight to the dynamics of the processes being observed rather then only considering the consequences of the processes. Stated another way, observing the relationships of the state variables of a group in a selected time frame rather than separately allows an observer to monitor the changes of the group moving toward equilibrium rather than just observing the group at an equilibrium.

It follows that an entropy measurements could be used in genetic engineering, biologic engineering, drug engineering and device engineering. By detecting consequences of treatments or therapies early, adjustments can be made to optimize the treatments or therapies to achieve the desired results.

Entropy evaluation is not only available for biological materials at the molecular or cellular levels, but also at organ, tissue, and system levels as well, because entropy provides a state variable relative to the changes in the group being observed. For example, blood is a group of similar cells that make up an organ of the body. The heart, the cardiovascular system, the liver, the kidney, the lungs, the brain, the skin, the bones, tissues, and essentially all organs and systems in the body are comprised of groups of similar cells that work together to form the living body. Each of these biological materials can be looked at independently or in combination with the other parts of the body. The appropriate measure of entropy depends on the groups or systems being studied.

There are at least two perspectives that derive utility from monitoring entropy. One perspective considers the normal or optimal entropy or entropy changes of a living thing, or a sub-set of it, at rest or during elevated activity. Deviations from a baseline indicate changes in the state of health of the living thing. This provides a diagnostic and prognostic tool that can be used to detect, correct and/or prevent unhealthy or sub-optimal conditions and to direct growth toward healthy or optimal conditions. The second perspective applies to intervention into the life process and the resulting consequences. The interventional action and the resulting response can be correlated and adjusted until the desired result is achieved. This perspective according to the present invention deals with the monitoring and adjustment of treatments or therapies.

One definition of entropy can be mathematically derived from the first and second laws of thermodynamics by making several assumption to simplify the equation. These assumptions are:

1. The "Heat" part of the total energy of a system or group is measured at constant volume.

2. The "Work" part of the total energy of the system or group is measured at constant entropy.

3. The volume of the group is equal to one.

In view of these assumptions and with the total energy of the system or group being constant, the entropy of a group is generally described as:

$$s = dP/dT$$

where:
s=entropy of the group
dP=change in pressure of the group or $P_{t1}-P_{t2}$
dT=change in temperature of the group or $T_{t1}14\ T_{t2}$
t1=time at measurement 1
t2=time at measurement 2

Although these assumptions do not agree with the nature of living materials, it is appreciated that corrections and compensations can be factored as required to increase the accuracy of the measurements for living materials. These assumptions however are satisfactory within the context of the present invention. Pressure and temperature measurements of a group made simultaneously in real time permit evaluation of the approximate entropy of the group in real time, by repeating the measurements and calculation for each point in time. The determined entropy value, or vital status value, can be displayed on a display device as a running value or can be monitored for treatment of life activity.

The calculated unit of measure (entropy) provides more information than either temperature in time or pressure in time alone or independently from each other, because entropy considers the relationship between temperature and pressure and changes over time for the group. As is defined by the laws of thermodynamics, pressure and temperature of a group are different measures of components of the total energy of the group and are relative to the arrangement and possible arrangements of the group. Pressure and temperature are functions of the entropy and total energy of the group.

Referring now in more detail to the drawings in which like parts have like identifiers, FIG. 1 illustrates a back side of a measuring and display apparatus 10 according to the present invention. The apparatus 10 includes a housing 12 with a bottom side 14 from which a temperature sensor 16 and a pressure transducer 18 extend. The temperature sensor 16 and the pressure transducer 18 bear against a skin surface of person wearing the apparatus on a wrist. This is accomplished by providing a pair of bands 20, 22 which attach on opposing sides of the housing 12. The bands 20, 22 have connectors at respective distal ends for wrapping around the wrist of the person using the apparatus 10 for measuring and displaying information about the person's health status. In the illustrated embodiment, the bands 20, 22 have respective patches 24, 26 of matingly engagable material such as Velcro brand hook-and-loop connector patches.

The temperature sensor 16 connects to a controller 30 that mounts within the housing 12. The controller 30 receives a signal from the sensor 16 representative of the temperature of the skin surface in contact with the sensor. The controller 30 also receives a signal from the pressure transducer 18 representative of the pressure measured by the transducer bearing against the skin surface of the person wearing the apparatus 10. The controller 30 connects to switches 32, 34, and 36. The switch 32 communicates a signal to the controller to start and stop the temperature and pressure monitoring by the apparatus 10. The switch 34 communicates a signal to the controller 30 to set the baseline indicator for the person using temperature and pressure data collected over a predetermined interval. In the illustrated embodiment, the data is collected over a ten second interval after the switch 34 is actuated. The switch 36 is used to cyclically change a display of measured temperature, pressure, or computed indicia based on the measured temperature and pressure, as discussed below.

Figure 2:
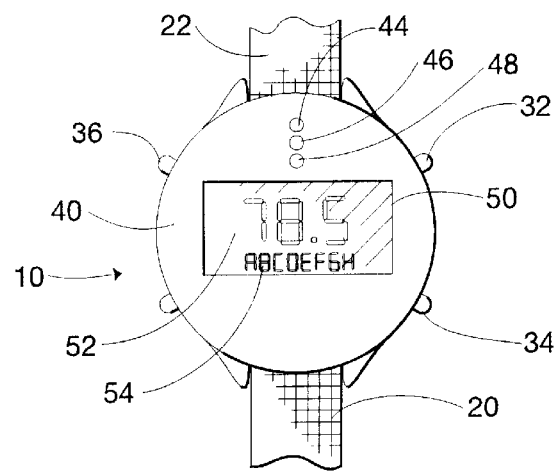
FIG. 2 illustrates a front view of the measuring and display apparatus shown in FIG. 1.

FIG. 2 is a front view of the apparatus 10 illustrating display features on a front face 40 of the apparatus. The front face 40 includes a plurality of status display lights 44, 46, and 48, for a purpose discussed below. A display screen 50 connects to the controller 30. The display screen 50 includes a numeric display portion 52 and a text display portion 54.

The apparatus 10 is used for example by a person exercising. The apparatus 10 is strapped onto the wrist portion of the exerciser with the bottom side 14 against the skin. The bands 20, 22 are joined together with the connectors 24, 26. The temperature sensor 16 and the pressure transducer 18 press against the skin surface. Preferably, the pressure transducer 18 bears against a portion of the wrist having a blood vessel. The temperature sensor 16 communicates a signal representative of the temperature of the skin to the controller 30. The pressure transducer 18 communicates a second signal representative of the sensed pressure to the controller 30. These signals are evaluated by the controller for computing the entropy of the exerciser. The switch 32 is actuated to communicates a signal to the controller to start the temperature and pressure monitoring by the apparatus 10. The controller 30 uses the temperature and pressure signals cooperatively with a clock to compute the changes in temperature and pressure over time. The computed changes in the temperature and pressure are then evaluated to compute the entropy measure. The display 50 displays in the numeric portion 52 either the temperature, the pressure, or the computed entropy measure, depending on the display selected using the switch 36. The text display 54 provides a text message appropriate for the particular data being displayed on the numeric portion 52. The switch 36 is selectively actuated to cycle through the displayable temperature, pressure, or entropy measure. At an appropriate time, the switch 34 is actuated, to set the computed entropy measure as a baseline value for the exerciser.

The controller 30 compares the baseline value with the computed entropy measure using the recent temperature and pressure signals. The baseline value is selectively the historical entropy of the measure system for the patient or the standard considered by health authorities as normal for persons or organs of similar characteristics, for example, age, weight, height, or gender. In the illustrated embodiment, one of the status display lights 44, 46, 48 is activated by the controller 30 to provide a visual indication of the computed entropy measure relative to the baseline value. In a preferred embodiment, the status display light 44 corresponds to a computed measure considered superior to the baseline value while the display light 48 corresponds to a computed measure considered as inferior to the baseline value. The display light 46 corresponds to a computed measure considered substantially equivalent to the baseline value. In a preferred embodiment, the particular display light 44, 46, or 48 is determined by the computed entropy measure being within a predetermined range of the baseline value, for example, within 10 percent above or below the baseline. If the difference between the computed entropy measure and the baseline value exceeds 10 percent of the baseline value, then the light 44 is activated. If the difference between the computed entropy measure and the baseline value is less than 10 percent of the baseline value, then the light 48 is activated. In the illustrated embodiment, the display lights 44, 46, 48 are disposed in a line which from the exerciser's view approximates a vertical line, to provide a further visual display of the computed entropy value relative to the baseline value. In another embodiment, the lights 44 and 46 are green while the light 48 is amber.

Figure 3:
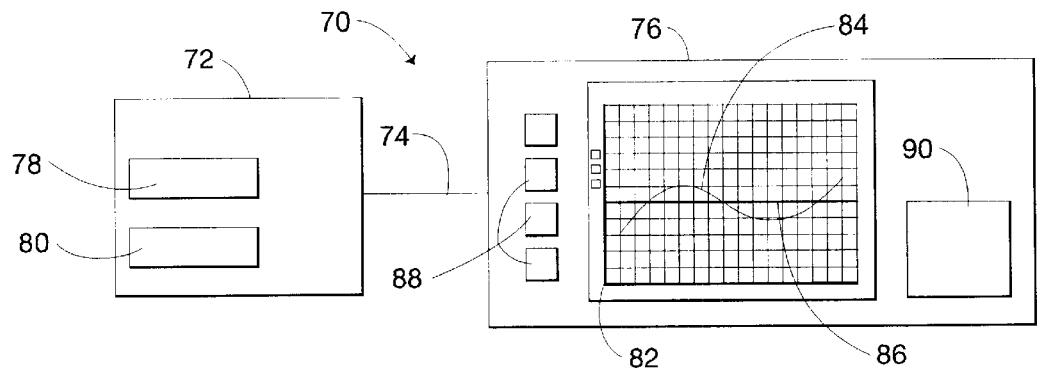
FIG. 3 illustrates a schematic diagram of an entropy measuring and display apparatus according to the present invention.

FIG. 3 illustrates a schematic diagram of a device 70 for measuring and monitoring the entropy state of a biologically active organ according to the present invention. The device 70 provides a catheter 72 connected by multi wire line 74 to a controller 76. The catheter 72 includes a temperature sensor 78, such as a thermistor, and a pressure transducer 80. These are conventionally disposed within lumens, or pathways, of the catheter 72 and communicate signals representative of the detected stimulus. The catheter 72 provides a probe for positioning the sensors in a biological material. In an alternate embodiment, the detecting sensors 78, 80 are disposed in a needle for positioning near an organ or biological material for observation of stimuli.

The signals from the temperature sensor 78 and the pressure sensor 80 communicate by the line 74 to the controller 76. The controller 76 includes a display device 82 for displaying selectively the particular measured stimulus 84, together with a baseline value 86. Switches 88 enable selective display of the measured temperature, pressure, and/or computed entropy of the measured biological material. The controller 76 further provides a data storage device 90 that includes baseline values for comparing the measured states. These baseline values include measured values of these state variables for the particular biological material (or patient) being monitored, as well as baseline values for biological materials of similar age, weight, height, gender, and baseline values for normative comparisons. In an alternate embodiment, a pair of the catheters 72 are provided for use in monitoring an organ based on changes upstream and downstream of fluid flow to the organ.

Figure 4:
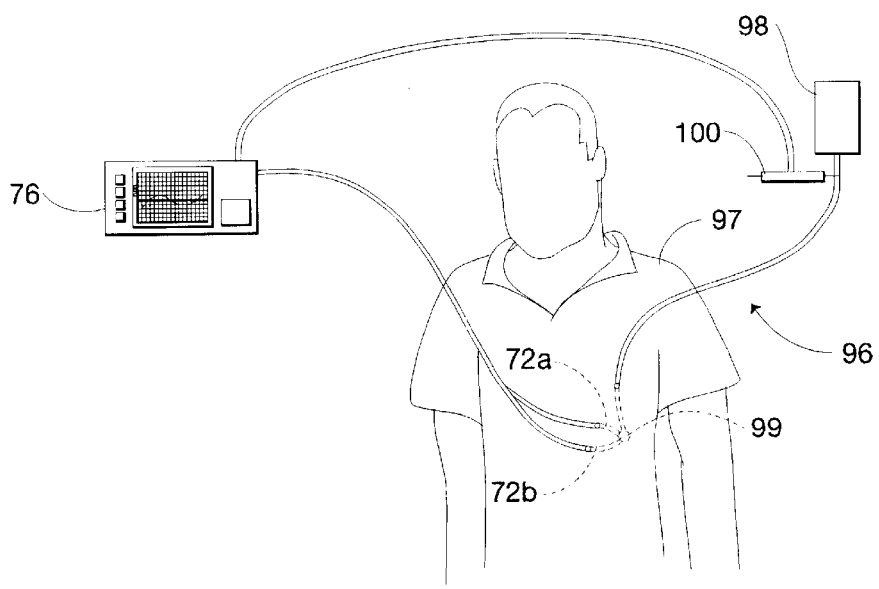
FIG. 4 illustrates a schematic diagram of the entropy measuring and display apparatus shown in FIG. 3 used with an adjustable medicant delivery for treatment of a patient.

FIG. 4 illustrates a schematic diagram of the entropy measuring and display apparatus 70 shown in FIG. 3 used with an adjustable medicant delivery device 96 for treatment of a patient 97. The medicant delivery device 96 has a supply 98 of a medicant for communication to the patient 97 at a selected rate. The controller 76 communicates a control signal to a rate controller 100, such as a variable valve, of the medicant delivery device 96. The control signal directs the rate controller 100 to modify the delivery of the medicant based on the measured entropy of the patient. Thereby the medicant flow is increased, decreased, or left unchanged in response to measuring and evaluating the entropy of the biological material under examination. In the practice of the present invention, the measurements are preferably made at one-tenth second intervals over a one-second period. For example, measurements can be made during successive beats of the heart of the patient. The present invention enables observation of the changes in the state of the patient during a heart beat, rather than the resulting steady-state value, which is useful for diagnosis and treatment.

For example, the liver performs a blood filtering function for living animals. As illustrated in FIG. 4, a pair of the catheters 72 are positioned in appropriate arterial and vascular blood vessels that supply and remove blood from the liver, The catheters 72 monitor and report the state variables of the incoming blood and the filtered blood. The determined entropy is displayed on the display 82. The controller 76 compares the entropy with baseline values. Based on these comparisons, the rate controller 100 is changed to adjust the flow of the medicant from the supply 98 to the patient 97. Comparing the entropy of the blood both before and after the filtration by the liver may provide useful information as to the health and vitality of the liver and the blood after passing through the liver of the patient being examined. As noted above, the entropy measurements are readily compared with measurements stored on a database. In a preferred embodiment, the entropy measurements are selectively compared with normal values for healthy persons (for example, selection based on common age, weight, height, or ranges of such, state of health, and/or gender) or previous measurements for the particular patient. In this manner, the vital status of the patient's liver (or other organ or system under evaluation) can be evaluated in terms of norms for all persons or for the particular patient. Diagnoses and treatment improvements are thereby provided by the present invention.

Figure 5:
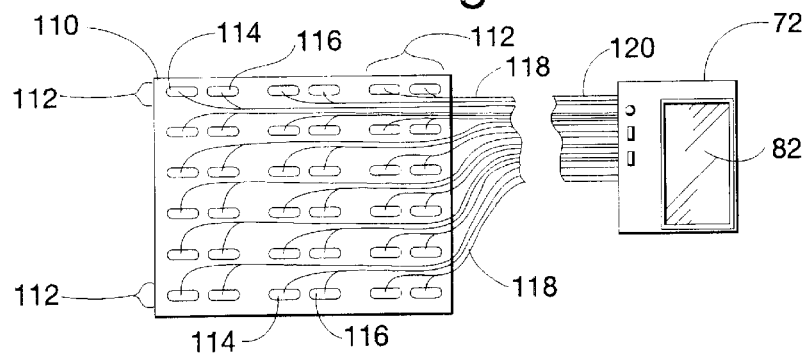
FIG. 5 illustrates a plan view of an entropy measuring sheet in accordance with the present invention.

FIG. 5 illustrates in plan view an entropy measuring sheet 110 in accordance with the present invention. The sheet 110 includes at least one pair 112 of sensors 114, 116 for detecting temperature and pressure stimuli respectively. In the illustrated embodiment, the sheet 110 includes a plurality of pairs 112 of the sensors 114, 116. Each pair 112 communicate via paired wire lines 118 in a web 120 to appropriate inputs to the controller 72. The controller 72 determines the vital status of the biological material across the sheet and displays determined values on the screen 82. For example, the sheet 110 can be placed over a wound, in order to track the progress of healing and to modify treatments.

It is thus seen that apparatus and methods of computing and evaluating biological activity is provided. While this invention has been described in detail with particular reference to the preferred embodiments thereof, the principles and modes of operation of the present invention have been described in the foregoing specification. The invention is not to be construed as limited to the particular forms disclosed because these are regarded as illustrative rather than restrictive. Moreover, modifications, variations and changes may be made by those skilled in the art without departure from the spirit and scope of the invention as described by the following claims.

What is claimed is:

1. An apparatus for monitoring a vital status indicator of a biological material, comprising:

a temperature sensor for sensing periodically a temperature of a biological material to be monitored for determining an indicator of a vital status of the biological material, said temperature sensor adapted to create a first electrical signal representative of the sensed temperature;

a pressure sensor for sensing periodically a pressure of the biological material substantially contemporaneously with the sensing by the temperature sensor and adapted to create a second electrical signal representative of the sensed pressure;

a signal transmitting pathway transmitting said first and second electrical signals to a signal receiver adapted to receive at least two of said first and second electrical signals for processing of the signals;

an evaluator that compares the difference in the two first electrical signals representative of temperatures sensed at a first time and a second time with the difference in the two second electrical signals representative of the pressures sensed, determine the indicator of the vital status as a representative value indicative of the state of the biological material; and a reporter for communicating the indicator of the vital status of the biological material, whereby the vital status of the biological material can be monitored.

2. The apparatus as recited in claim 1, further comprising a data storage device containing baseline values for comparing with the determined vital status.

3. The apparatus as recited in claim 2, wherein the baseline values are selected from a group comprising measured values for a selected patient, values based on ranges of ages, weights, heights, and gender, and normative values for the biological material.

4. The apparatus as recited in claim 2, wherein the reporter comprises a display device for communicating a visual representation of the determined vital status and the baseline value.

5. The apparatus as recited in claim 2, further comprising:

a medicant delivery apparatus for communicating a medicant from a supply of the medicant to a patient; and a communicator communicating a signal representative of a medicant delivery rate to the medicant delivery apparatus based on the comparison of the determined vital status and the baseline value, whereby the flow of the medicant from the supply to the patient is adjusted.

6. The apparatus as recited in claim 1, wherein the sensors are contained within a catheter.

7. The apparatus as recited in claim 1, wherein the sensors are contained in a probe.

8. The apparatus as recited in claim 1, wherein the sensors are contained in a sheet for overlying the biological material for sensing the temperature and the pressure thereof.

9. The apparatus as recited in claims 8, wherein the sheet includes a plurality of spaced-apart pairs of temperature and pressure sensors for communicating measurements of stimuli across a surface covered by the sheet.

10. A method of diagnosing the vital status of a biological material, comprising the steps of:
   (a) providing a temperature sensor for sensing periodically a temperature of a biological material to be monitored for determining an indicator of a vital status of the biological material, said temperature sensor adapted to create a first electrical signal representative of the sensed temperature;
   (b) providing a pressure sensor for sensing periodically a pressure of the biological material and adapted to create a second electrical signal representative of the sensed pressure substantially contemporaneously with the sensing by the temperature sensor;
   (c) communicating by a signal transmitting pathway said first and second electrical signals to a signal receiver adapted to receive at least two of said first and second electrical signals for processing of the signals;
   (d) comparing the difference in the two first electrical signals representative of temperatures sensed at a first time and a second time with the difference in the two second electrical signals representative of the pressures sensed, to determine the indicator of the vital status as a representative value indicative of the state of the biological material; and
   (e) reporting the indicator of the vital status of the biological material, whereby the vital status of the biological material can be monitored.

11. The method as recited in claim 10, further comprising the steps of:
   recording the indicator determined at a first period of time;
   determining the indicator for a second subsequent period;
   comparing the indicators for the first and second periods.

12. The method as recited in claim 10, further comprising the step (f) comparing the determined vital status indicator with a baseline value.

13. The method as recited in claim 12, wherein the baseline value is selected from a group comprising measured values for a selected patient, values based on ages, weights, heights, and gender, and normative values for the biological material.

14. The method as recited in claim 12, further comprising the step of adjusting a delivery of a medicant based on the comparison step (f).

15. The method as recited in claim 10, wherein the reporting step (e) comprises displaying a realtime image of the determined vital status indicator and the baseline value.

* * * * *